United States Patent [19]

Braun

[11] 4,265,928
[45] May 5, 1981

[54] ANTI-THROMBOGENIC RETENTIVE CATHETER

[75] Inventor: Bernd Braun, Melsungen, Fed. Rep. of Germany

[73] Assignee: Intermedicat GmbH, Emmenbrucke, Switzerland

[21] Appl. No.: 78,918

[22] Filed: Sep. 26, 1979

[30] Foreign Application Priority Data

Oct. 6, 1978 [CH] Switzerland ........................ 10439/78

[51] Int. Cl.³ .............................................. B05D 3/06
[52] U.S. Cl. .............................................. 427/2; 3/1.4
[58] Field of Search ................................. 3/1.4; 427/2

[56] References Cited

U.S. PATENT DOCUMENTS

| 3,585,647 | 6/1971 | Gajewski | 3/1.4 |
| 3,663,288 | 5/1972 | Miller | 3/1.4 |
| 3,695,921 | 10/1972 | Shepherd | 427/2 |
| 3,886,947 | 6/1975 | Sawyer | 3/1.4 |
| 4,055,682 | 10/1977 | Merrill | 427/2 |

Primary Examiner—Sam Silverberg
Attorney, Agent, or Firm—Merriam, Marshall & Bicknell

[57] ABSTRACT

An anti-thrombogenic retentive catheter with a negatively-charged surface is manufactured by providing it with a negatively-charged coating. The coating can be applied by immersing the catheter, at least once, into pyridine or a toluol/tetrahydrofuran solution of a copolymerizate of ethylene with acrylic acid, or esters or salts of the copolymerizate and, after the last immersion, by drying the coating until no solvent is detectable.

9 Claims, No Drawings

ANTI-THROMBOGENIC RETENTIVE CATHETER

This invention relates to catheters.

It has been known that retentive catheters made of polyvinylchloride, polyethylene with low available electron density, and synthetic materials with positively-charged molecular groups, have a particularly strong interaction with blood substances having an electronegative surface charge. The interaction between positively-charged, or neutral, material surfaces and thrombocytes apparently leads to a complicated coagulation mechanism, namely, the thrombi formation, as can be shown by means of raster electron-microscopic pictures. When sufficiently large, the blood clots and thrombi can detach, enter the blood circulation, and lead to life-threatening thrombosis in lungs and brain.

From the literature, e.g., Sawyer, Trans. Amer. Soc. Artif. Organs, Volume XVI, page 1, 1970, it is known, furthermore, that some synthetic materials, in particular those with negatively-charged molecular groups, such as ethylene-acrylic acid copolymerizates (EAA) and their known esters and salts; synthetic materials which contain crotonic acid as copolymers; sulfonated synthetic materials which contain $SO_3H$ groups; and synthetic materials which are layered with the $SO_3H$ group containing heparin, show an electro-negative charge, and catheters which have been manufactured from these synthetic materials do not induce the above pathological features leading to thrombosis.

A suitable method for ascertaining the electro-negative nature of individual synthetic material surfaces is through analysis of the zeta potential.

The described polymeric materials, however, possess a disadvantage in that they adhere extemely well, under manufacturing conditions commonly used for thermoplastics, to manufacturing apparatus used for shaping the materials. Thus, the extrusion of fine, or small, tubes of a diameter of 0.5 to 6 mm suitable for catheters is very difficult, and almost practically impossible.

Even though they are manufactured with difficulty, the resulting tubes are hardly true-to-size. The non-uniform tubes, when in contact with blood, evidence the beneficial characteristics of the above-mentioned materials charged with negative potential but, in practice, they are useless for a clinical application because of their relatively great hardness and stiffness. To avoid injuries to a vessel wall when a catheter is inserted, catheter materials, in general, have been sought which have a Shore hardness A of 50 to 80. However, catheters of ethylene-acrylic acid polymerizates, which have a Shore hardness D from 50 to 60, are too hard for use as catheters without the coating.

My tests, and tests carried out in practice, surprisingly have shown that it is possible to obtain the desired anti-thrombogenic characteristics and to reduce the danger of thrombosis when catheterizing, by coating catheters, and especially the polyvinylchloride (PVC) soft catheters, and the polyethylene (PE) catheters which have been used up to now, with a thin coating of an ethylene-acrylic acid copolymerizate (EAA), or an ester or salt of the copolymerizate.

The coating can be applied as a single layer or as a plurality of layers. The catheter should be cleaned first to remove any lubricant from the surface.

A suitable way to apply the coating is by use of a solvent solution of the ethylene-acrylic acid copolymerizate, or ester or salt of the copolymerizate.

The solution can be applied by dipping or immersing the catheter in the solution, or it can be applied by any other suitable means, such as spraying.

A suitable solvent for the copolymerizate is pyridine or a mixture of toluol and tetrahydrofuran. Other solvents, or mixtures of solvents, can be used.

After the solution is applied, the catheter is heated to dry the coating. If two or more layers are applied, the preceding layer should only be dried until it is tacky and then the subsequent layer should be deposited. However, after all the layers are applied, the coating should be dried until no detectable amount of solvent is released by the coating.

The completed coated catheter can then be sterilized for use.

The following example is presented to illustrate the invention.

EXAMPLE

The PVC and PE catheters, completely cleaned of lubricants, are immersed into a 1% solution of EAA in toluol-tetrahydrofuran 1:1 and are slightly dried, at 40° C., in a heating chamber. While they are still in tacky condition, the catheters are again shortly immersed in a solution of 0.1% EAA in toluol-tetrahydrofuran 1:1 and thereupon dried, at 60° C., in the heating chamber until all solvents have evaporated and are no longer chemically and physiologically detectable, and the catheter surface is completely dry. The catheters are sterilized for clinical use by means of gamma rays, at about 2.5 Mrad, using a single treatment sterile packaging method.

The catheters treated as described and implanted into the blood circulation, in animal and clinical tests, showed the desired anti-thrombogenic characteristics and reduced, to a large extent, the danger of thrombosis when catheterizing.

The foregoing detailed description has been given for clearness of understanding only, and no unnecessary limitations should be understood therefrom, as modifications will be obvious to those skilled in the art.

What is claimed is:

1. A method of producing an anti-thrombogenic retentive catheter with a negatively charged surface, which comprises coating a polyvinylchloride or polyethylene catheter with a solution in pyridine, or a solvent mixture of toluol and tetrahydrofuran, of a copolymerizate of ethylene with acrylic acid, or an ester or salt of the copolymerizate.

2. A method according to claim 1 in which the coating is dried, after application, until no solvent is detectable.

3. A method according to claim 1 in which the catheter is cleaned of lubricants before the coating is applied.

4. A method according to claim 1 in which the coating comprises a plurality of layers, each layer is applied as a solvent solution of the copolymerizate, and subsequent layers are applied to prior layers while tacky.

5. A method according to claim 1 in which the coating is applied by immersing the catheter in the solvent solution.

6. A method of producing an anti-thrombogenic retentive catheter with a negatively-charged surface, which comprises coating the catheter surface with a solution in pyridine, or a solvent mixture of toluol and tetrahydrofuran, of a copolymerizate of ethylene with acrylic acid, or an ester or salt of the copolymerizate.

7. A method of producing an anti-thrombogenic retentive catheter with a negatively-charged surface, which comprises coating the catheter surface with a plurality of layers of a copolymerizate of ethylene with acrylic acid, or an ester or salt of the copolymerizate, with each layer being applied as a solvent solution of the copolymerizate, and subsequent layers are applied to prior layers while tacky.

8. A method according to claim 7 in which the coating of the copolymerizate is applied as a solution in pyridine or a solvent mixture of toluol and tetrahydrofuran.

9. A method according to claim 7 in which the catheter is made from a member of the group consisting of polyvinylchloride and polyethylene.

* * * * *